United States Patent
Kim et al.

(10) Patent No.: US 10,041,908 B2
(45) Date of Patent: Aug. 7, 2018

(54) VOLATILE ORGANIC COMPOUND SENSOR

(71) Applicant: INDUSTRY-ACADEMIC COOPERATION FOUNDATION YONSEI UNIVERSITY, Seoul (KR)

(72) Inventors: Jong Baeg Kim, Goyang-si (KR); Kyounghoon Lee, Seoul (KR); Yunsung Kang, Busan (KR)

(73) Assignee: INDUSTRY-ACADEMIC COOPERATION FOUNDATION YONSEI UNIVERSITY, Seoul (KR)

( * ) Notice: Subject to any disclaimer, the term of this patent is extended or adjusted under 35 U.S.C. 154(b) by 51 days.

(21) Appl. No.: 15/263,909

(22) Filed: Sep. 13, 2016

(65) Prior Publication Data
US 2017/0074828 A1    Mar. 16, 2017

(30) Foreign Application Priority Data
Sep. 14, 2015   (KR) .................. 10-2015-0129893

(51) Int. Cl.
G01N 27/66    (2006.01)
(52) U.S. Cl.
CPC ................... *G01N 27/66* (2013.01)
(58) Field of Classification Search
CPC .................................................. G01N 27/66
See application file for complete search history.

(56) References Cited

U.S. PATENT DOCUMENTS

| 5,393,979 A | * | 2/1995 | Hsi ..................... G01N 27/66 250/379 |
| 5,578,271 A | * | 11/1996 | Simon ................ G01N 27/66 422/54 |

(Continued)

FOREIGN PATENT DOCUMENTS

| JP | 2010-256165 A | 11/2010 |
| JP | 2014-215155 A | 11/2014 |

(Continued)

OTHER PUBLICATIONS

KIPO Office Action for Korean Application No. 10-2015-0129893 dated Dec. 20, 2016.

*Primary Examiner* — Walter L Lindsay, Jr.
*Assistant Examiner* — Milton Gonzalez
(74) *Attorney, Agent, or Firm* — LRK Patent Law Firm

(57) ABSTRACT

A VOC detection sensor includes: a photoemission acceleration unit including a first electrode and a second electrode spaced apart from each other to face each other and a power source unit forming an electric field between the first electrode and the second electrode, photoemission means disposed within a space formed by the first electrode and second electrode of the photoemission acceleration unit and emitting photoelectrons, a light source supplying light energy by which the photoemission means emits photoelectrons, and an ammeter measuring the amount of charges flowing between the first electrode and the second electrode, wherein VOCs in the space between the first electrode and the second electrode are ionized through a collision against photoelectrons accelerated by the photoemission acceleration unit, and the ammeter detects a concentration of the VOCs by measuring the amount of charges formed by the ionized VOCs between the first electrode and the second electrode.

14 Claims, 2 Drawing Sheets

(56) References Cited

U.S. PATENT DOCUMENTS

| | | | | |
|---|---|---|---|---|
| 5,773,833 A * | 6/1998 | Hsi | ............... | G01N 27/64 250/379 |
| 6,225,633 B1 * | 5/2001 | Sun | ............... | G01N 27/66 250/281 |
| 6,313,638 B1 * | 11/2001 | Sun | ............... | G01N 27/66 324/464 |
| 6,320,388 B1 * | 11/2001 | Sun | ............... | G01N 27/66 250/281 |
| 6,627,897 B1 * | 9/2003 | Francke | ............ | G01T 1/185 250/374 |
| 6,646,444 B2 * | 11/2003 | Dolgov | ............ | G01N 27/66 250/382 |
| 6,734,435 B2 * | 5/2004 | Sun | ............... | G01N 27/66 250/281 |
| 6,967,485 B1 * | 11/2005 | Hsueh | .............. | G01N 27/64 250/382 |
| 7,046,012 B2 * | 5/2006 | Dean | ............... | G01N 27/62 324/459 |
| 7,180,076 B2 * | 2/2007 | Haverstick | ........ | G01N 27/66 250/372 |
| 2012/0136268 A1 * | 5/2012 | Li | ............... | G01N 27/66 600/532 |

FOREIGN PATENT DOCUMENTS

| | | |
|---|---|---|
| KR | 10-2008-0111444 A | 12/2008 |
| KR | 10-2009-0131513 A | 12/2009 |

\* cited by examiner

VOLATILE ORGANIC COMPOUND SENSOR

CROSS REFERENCE TO RELATED APPLICATION

The present application claims the benefit of Korean Patent Application No. 10-2015-0129893 filed in the Korean Intellectual Property Office on Sep. 14, 2015, the entire contents of which are incorporated herein by reference.

BACKGROUND OF THE INVENTION

1. Field of the Invention

The present invention relates to a sensor for detecting volatile organic compounds and, more particularly, to a volatile organic compound sensor of an ionization method, which adopts a cheap light source and uses accelerated photoemission electrons.

2. Description of the Related Art

Volatile organic compounds (VOC) whose amount is suddenly increased in a living environment have a bad influence on the human body in many aspects, such as the induction of cancer and skin diseases such as atopic dermatitis.

In general, such VOCs are present in a gaseous state at normal temperature and in atmospheric pressure. In Clean Air Conservation Act of Korea, petrochemicals, organic solvents and other materials of hydrocarbon series officially announced by the Minister of Environment have been defined as the VOCs, but are not limited thereto. The VOCs may include all of organic compounds ionized in energy of a specific amount (e.g., 9 eV) or higher.

As the emission quantity of VOCs increases, a need to detect VOCs also increases. In general, a conventional VOC sensor for detecting VOCs may be divided into a photoionization (PID) method and a semiconductor type resistance change method. The photoionization method has a disadvantage in that a production cost is high because an expensive light source is used. Furthermore, the semiconductor type resistance change method has a problem in that sensitivity is very low compared to the photoionization method. Accordingly, there is a need for the development of a VOC sensor of a new method, which is cheap while maintaining a specific level or more of sensitivity.

SUMMARY OF THE INVENTION

Accordingly, the present invention has been made keeping in mind the above problems occurring in the prior art, and an object of the present invention is to provide a VOC detection sensor of a new structure, which can use a cheap light source.

In accordance with an embodiment of the present invention, a VOC detection sensor includes a photoemission acceleration unit configured to include a first electrode and a second electrode spaced apart from each other in such a way as to face each other and a power source unit forming an electric field between the first electrode and the second electrode, photoemission means disposed within a space formed by the first electrode and second electrode of the photoemission acceleration unit and configured to be capable of emitting photoelectrons, a light source configured to supply light energy by which the photoemission means is capable of emitting photoelectrons, and an ammeter configured to measure the amount of charges flowing between the first electrode and the second electrode, wherein VOCs accommodated in the space between the first electrode and the second electrode are ionized through a collision against photoelectrons accelerated by the photoemission acceleration unit, and the ammeter detects a concentration of the VOCs by measuring the amount of charges formed by the ionized VOCs between the first electrode and the second electrode.

In this case, according to another embodiment of the present invention, an electrode that belongs to the first electrode and the second electrode and is connected to the cathode of the power source unit includes the photoemission means.

Furthermore, the light source provides light of a wavelength by which the photoemission means emits photoelectrons, but does not directly ionize the VOCs.

Furthermore, the photoemission acceleration unit may form the electric field accelerating the photoelectrons so that the electric field ionizes the VOCs, but has energy of a range in which nitrogen and oxygen within air are not ionized, for example so that the photoelectrons have energy in the range of 9.3 to 12 eV.

In accordance with another embodiment of the present invention, a VOC detection sensor includes a light source, a first electrode and a second electrode configured to form an electric field through an interaction with the first electrode and provided as the second migration channel of light generated from the light source, an insulating structure configured to separate the first electrode and the second electrode so that the first electrode and the second electrode are insulated, photoemission means disposed within a spaced formed between the first electrode and the second electrode and configured to emit photoelectrons for ionizing VOCs by the light, and a substrate disposed between the second electrode and the light source, provided as a first migration channel of the light, and configured to have the light source installed or formed in the substrate.

In this case, the light source may include an LED grown over the substrate.

Furthermore, the second electrode may include the photoemission means.

Furthermore, the insulating structure may be made of a glass material, and a VOC migration channel may be formed between the first electrode and the second electrode by the insulating structure.

Furthermore, the second electrode and the substrate may be made of a transparent material.

In this case, the light source may provide light of a wavelength by which the photoemission means emits photoelectrons, but does not directly ionize the VOCs, for example, light of a wavelength in the range of 230 nm to 260 nm.

Furthermore, the VOC detection sensor may further include a power source unit configured to have an anode and a cathode connected to the first electrode and the second electrode, respectively.

DETAILED DESCRIPTION

Figure 1:
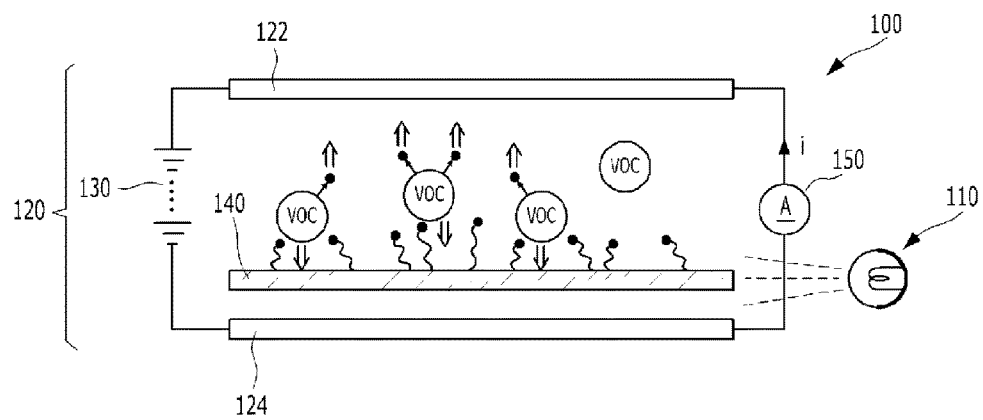
FIG. 1 is a diagram showing a schematic configuration of a VOC detection sensor according to an embodiment of the present invention.

Some exemplary embodiments of the present invention are described in detail with reference to the accompanying drawings.

It is to be noted that in assigning reference numerals to elements in the drawings, the same reference numerals denote the same elements throughout the drawings even in cases where the elements are shown in different drawings. Furthermore, in describing the embodiments of the present invention, a detailed description of the known functions and constitutions will be omitted if it is deemed to make the gist of the present invention unnecessarily vague.

Furthermore, the size or shape of elements shown in the drawings may have been enlarged for the clarity of a description and for convenience' sake. Furthermore, terms specifically defined by taking into consideration the configuration and operation of the present invention are merely for illustrating embodiments of the present invention and do not limit the scope of the present invention.

FIG. 1 is a diagram showing a schematic configuration of a VOC detection sensor 100 according to an embodiment of the present invention. The VOC detection sensor 100 according to an embodiment of the present invention is described in detail below.

The VOC detection sensor 100 according to an embodiment of the present invention includes a photoemission acceleration unit 120, photoemission means 140, a light source 110, and an ammeter 150.

The photoemission acceleration unit 120 includes a first electrode 122 and a second electrode 124 spaced apart from each other and disposed to face each other. The photoemission acceleration unit 120 further includes a power source unit 130 for forming an electric field between the first electrode 122 and the second electrode 124.

Furthermore, the photoemission means 140 is disposed within a space formed by the first electrode 122 and second electrode 124 of the photoemission acceleration unit 120. The photoemission means 140 emits photoelectrons by light energy emitted by the light source 110.

Furthermore, the ammeter 150 measures the amount of charges, that is, the intensity of current flowing between the first electrode 122 and the second electrode 124.

A gas (or air) including VOCs to be detected is accommodated in the space between the first electrode 122 and the second electrode 124 or flows between the first electrode 122 and the second electrode 124. An operational principle of the VOC detection sensor 100 configured as described above according to an embodiment of the present invention is described below.

Light radiated by the light source 110 generates a photoelectric effect on a surface of the photoemission means 140, and thus the photoemission means 140 emits photoelectrons. The photoemission means 140 may be made of various metal materials that generate a photoelectric effect. For example, potassium or sodium may be used the various metal materials.

Photoelectrons emitted from the photoemission means 140 are accelerated by a force in the direction from a cathode to an anode under the influence of an electric field formed between the first electrode 122 and the second electrode 124. The accelerated photoelectrons have gradually increasing energy in proportion to an increasing speed thereof. When energy of the electrons reaches a specific level or more, the outermost electrons of VOCs are emitted when the electrons collide against the VOCs. That is, the VOCs are ionized. The emitted outermost electrons move to an electrode (e.g., the first electrode in FIG. 1) that belongs to the first electrode 122 and the second electrode 124 and that has the property of the anode. The VOCs that have become positive ions because they have emitted the electrons move to an electrode (e.g., the second electrode in FIG. 1) having the property of the cathode.

The VOCs ionized as described above cause electric charges to be migrated in the first electrode 122 and the second electrode 124. A flow of the ionized VOCs changes the amount of current flowing between the first electrode 122 and the second electrode 124. A change of the amount of current by the ionized VOCs is proportional to a concentration of VOCs included in a gaseous sample. As a result, a concentration of VOCs can be detected by measuring a change of current using the ammeter 150.

In this case, the light source 110 used in the VOC detection sensor 100 according to an embodiment of the present invention causes the photoemission means 140 to emit photoelectrons, but provides light of a wavelength that does not directly ionize VOCs, for example, light of a wavelength in the range of 230 nm to 260 nm. That is, the light source 110 according to an embodiment of the present invention merely helps the photoemission means 140 to generate a photoelectric effect. Energy that actually ionizes VOCs is supplied by an electric field that accelerates the emitted photoelectrons not by the light source 110.

In a conventional technology, an organic lamp for radiating light of high energy is used as a light source. Light of high energy having a short wavelength of about 110 nm radiated by such an organic lamp light source directly ionizes VOCs. Accordingly, a conventional technology has high power consumption because it directly ionizes VOCs by radiating light of high energy. In contrast, the light source 110 according to an embodiment of the present invention is much advantageous in terms of energy consumption of a light source and the price of the light source itself because light of low energy has only to be radiated to the photoemission means 140 to the extent that a photoelectric effect may occur.

Furthermore, in order to accelerate photoelectrons, the intensity of the electric field formed between the first electrode 122 and the second electrode 124 may be set to have minimum energy to the extent that photoelectrons can ionize VOCs.

The most representative VOCs may include four types of VOCs (BTEX), such as benzene, toluene, ethylbenzene, and xylene. Ionized energies of the VOCs are as follows: benzene 9.25 eV, toluene 8.82 eV, ethylbenzene 8.76 eV, p-xylene 8.45 eV, and m, o-xylene 8.56 eV. Accordingly, if the intensity of the electric field is about 9.3 eV, most of VOCs can be ionized.

The upper limit of the intensity of the electric field may be properly determined because power consumption increases if the intensity of the electric field is too great. Ionized energies of nitrogen and oxygen that occupy most of air may be used as a criterion for the upper limit. The reason for this is that the ionized energies of nitrogen and oxygen are 15.58 eV and 12.08 eV, respectively, and are higher than those of the VOCs and nitrogen and oxygen do not need to be ionized when the VOCs are detected. Accordingly, the upper limit of the intensity of the electric field may be set to about 12 eV or lower.

Figure 2:
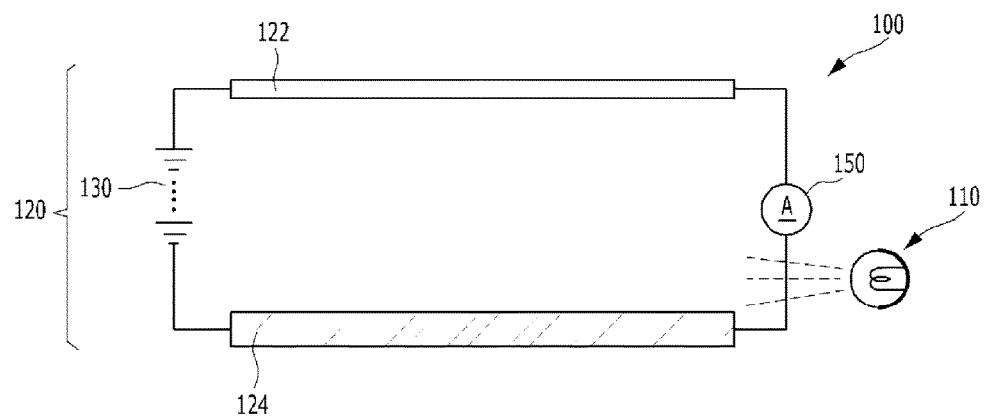
FIG. 2 is a diagram showing a schematic configuration of a VOC detection sensor according to another embodiment of the present invention.

FIG. 2 shows another embodiment of the VOC detection sensor 100.

The VOC detection sensor 100 of FIG. 2 has the same configuration as that of FIG. 1 except that an electrode connected to the cathode of the power source unit 130, that is, the second electrode 124 itself in FIG. 2, is made of the same metal material as the photoemission means 140. If the second electrode 124 is made of a metal material that generates a photoelectric effect as described above, it is advantageous from a viewpoint of fabrication because the number of elements can be reduced.

Figure 3:
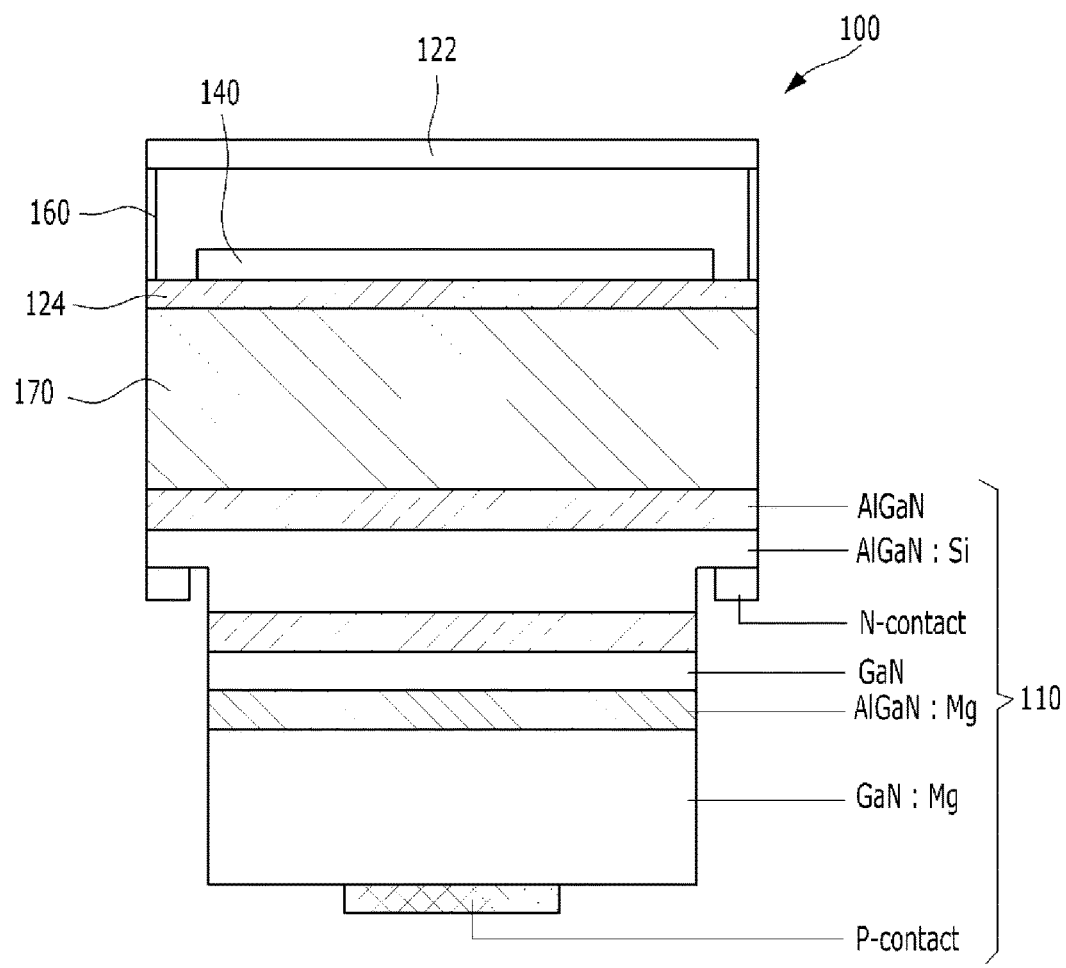
FIG. 3 is a diagram showing a structure in which a VOC detection sensor according to an embodiment of the present invention has been fabricated in a bundle on a substrate having an LED light source formed therein.

FIG. 3 shows an embodiment of the VOC detection sensor 100 in which the light source 110 is disposed on one side of a substrate 170 and the first/second electrodes 122 and 124 and the photoemission means 140 are disposed on the other side of the substrate 170.

The VOC detection sensor 100 of FIG. 3 has the same operational principle as that of FIGS. 1 and 2, and thus the structural characteristics of the embodiment of FIG. 3 are chiefly described. It is to be noted that the power source unit 130 and the ammeter 150 have been omitted in FIG. 3 in order to clearly illustrate the basic structure of the VOC detection sensor 100. The construction including the power source unit 130 and the ammeter 150 will be evidently understood with reference to FIGS. 1 and 2.

The light source 110 is disposed on one side of the substrate 170. Furthermore, the first electrode 122 and the second electrode 124 provided as a second migration channel of light generated from the light source 110 while forming an electric field through an interaction with the first electrode 122 are disposed on the other side of the substrate 170. In this case, an insulating structure 160 separates the first electrode 122 and the second electrode 124 while supporting them so that the first electrode 122 and the second electrode 124 are insulated. Furthermore, the photoemission means 140 is disposed within the space formed between the first electrode 122 and the second electrode 124.

That is, in the VOC detection sensor 100 of FIG. 3, the light source 110 is disposed on one side of the substrate 170 and another element for detecting VOCs is disposed on the other side of the substrate 170. Such a structure may be said to be a structure advantageous to stack the VOC detection sensor 100 using the substrate 170 as a support structure.

In particular, if an LED formed by growing it on the substrate 170, that is, a vertical type LED lamp, is used as the light source 110, a plurality of the VOC detection sensors 100 can be fabricated on a single substrate 170 in a lump through a disposition process. Accordingly, the VOC detection sensors 100 can be made compact and such a method is very suitable for mass production.

In the configuration of FIG. 3, the substrate 170 serves as a first migration channel through which light has to first pass because the substrate 170 is interposed between the second electrode 124 and the light source 110. Furthermore, the second electrode 124 has to function as the second migration channel in order for the light passing through the substrate 170 to reach the photoemission means 140. Accordingly, a hole through which the light can pass may be formed in each of the substrate 170 and the second electrode 124, but the substrate 170 and the second electrode 124 may be made of a transparent material in terms of manufacturing convenience and in order to secure a sufficient amount of light that will reach the photoemission means 140.

The transparent substrate 170 may be made of sapphire. FIG. 3 shows an embodiment in which the LED light source 110 is directly formed by growing (or depositing) a gallium nitride LED on the substrate 170 made of sapphire and etching the gallium nitride LED. Furthermore, a known transparent electrode, such as ITO, graphene, carbon nanotubes, or conductive polymer, may be used as the second electrode 124.

Furthermore, the insulating structure 160 is provided between the first electrode 122 and the second electrode 124. The insulating structure 160 forms the space between the first electrode 122 and the second electrode 124 and also supports them so that the first electrode 122 and the second electrode 124 are insulated. The insulating structure 160 may be made of various insulating materials including a glass material.

Furthermore, the insulating structure 160 functions to form the space in which a gaseous sample including VOCs is accommodated or a channel through which the gaseous sample moves between the first electrode 122 and the second electrode 124 in addition to the insulation purpose. Accordingly, if the insulating structure 160 forms the space in which the gaseous sample including VOCs is accommodated, it may have a wall structure that closes down the space between the first electrode 122 and the second electrode 124. If the insulating structure 160 forms the channel through which the gaseous sample moves, it may have a wall structure or a pillar structure that forms an inlet and an exit.

Furthermore, the photoemission means 140 disposed within the space formed between the first electrode 122 and the second electrode 124 may be located in the middle of the space or may be provided on the second electrode 124 using various methods, such as adhesion, coating, and plating. Furthermore, FIG. 3 shows an embodiment in which the photoemission means 140 has closely adhered to the second electrode 124, but the photoemission means 140 itself may become the second electrode 124 itself as described above with reference to FIG. 2.

The VOC detection sensor configured as described above according to an embodiment of the present invention has advantages in that it can lower the price of the sensor and consumes low power because a cheap light source that emits light of a relatively long wavelength compared to a conventional light source is used and VOCs can be ionized by accelerating photoelectrons emitted by a photoelectric effect with a voltage of several volts or several tens of volts.

Furthermore, the VOC detection sensor that is advantageous in terms of durability can be provided because a chemically stable material having a low work function is used as the photoemission means.

Furthermore, the VOC detection sensor according to an embodiment of the present invention has advantages in that it can be made compact and is very suitable for mass production because an LED is used as a light source and the VOC detection sensors can be fabricated in a lump through a disposition process.

While some exemplary embodiments of the present invention have been described with reference to the accompanying drawings, those skilled in the art may change and modify the present invention in various ways without departing from the essential characteristic of the present invention.

Accordingly, the disclosed embodiments should not be construed as limiting the technical spirit of the present invention, but should be construed as illustrating the technical spirit of the present invention.

The scope of the technical spirit of the present invention is not restricted by the embodiments, and the scope of the present invention should be interpreted based on the following appended claims. Accordingly, the present invention should be construed as covering all modifications or variations derived from the meaning and scope of the appended claims and their equivalents.

What is claimed is:

1. A volatile organic compound (VOC) detection sensor, comprising:
 a photoemission acceleration unit comprising:
  a first electrode and a second electrode spaced apart from each other in such a way as to face each other, and
  a power source unit generating an electric field between the first electrode and the second electrode;
 photoemission material made of metal for emitting photoelectrons;
 a light source supplying light energy by which the photoemission material emits the photoelectrons; and
 an ammeter measuring an amount of electric charges flowing between the first electrode and the second electrode,
 wherein the photoemission material is disposed within a spaced formed by the first and second electrodes of the photoemission acceleration unit, or the second electrode is made of the photoemission material,
 wherein VOCs accommodated in the space between the first electrode and the second electrode are ionized through collision against the photoelectrons which are emitted from the photoemission material by the light source and accelerated by the photoemission acceleration unit,
 wherein the ammeter detects a concentration of the VOCs by measuring an amount of electric charges generated by the ionized VOCs between the first electrode and the second electrode, and
 wherein the light source provides light of a wavelength by which the photoelectrons are emitted from the photoemission material while the VOCs are not directly ionized.

2. The VOC detection sensor of claim 1, wherein the second electrode is connected to a cathode of the power source unit.

3. The VOC detection sensor of claim 1, wherein the photoemission acceleration unit generates the electric field for accelerating the photoelectrons so that the electric field has an energy range in which the VOCs are ionized while nitrogen and oxygen contained in air are not ionized.

4. The VOC detection sensor of claim 3, wherein the photoemission acceleration unit generates the electric field so that the photoelectrons have an energy of 9.3 to 12 eV.

5. A volatile organic compound (VOC) detection sensor, comprising:
 a light source;
 a first electrode and a second electrode generating an electric field, the second electrode being provided as a second migration channel of light generated from the light source;
 an insulating structure separating the first electrode and the second electrode from each other so that the first electrode and the second electrode are insulated;
 photoemission material made of metal for emitting photoelectrons to ionize VOCs by the light; and
 a substrate disposed between the second electrode and the light source, provided as a first migration channel of the light, and having the light source installed or formed thereon,
 wherein the photoemission material is disposed within a spaced formed by the first and second electrodes, or the second electrode is made of the photoemission material, and
 wherein the light source provides light of a wavelength by which the photoelectrons are emitted from the photoemission material while the VOCs are not directly ionized.

6. The VOC detection sensor of claim 5, wherein the light source comprises a light-emitting diode (LED grown and formed over the substrate.

7. The VOC detection sensor of claim 5, wherein the insulating structure is made of a glass material.

8. The VOC detection sensor of claim 5, wherein a VOC migration channel is formed between the first electrode and the second electrode by the insulating structure.

9. The VOC detection sensor of claim 5, wherein the second electrode and the substrate are made of a transparent material.

10. The VOC detection sensor of claim 5, wherein the light source provides light of a wavelength of 230 nm to 260 nm.

11. The VOC detection sensor of claim 5, further comprising a power source unit having an anode and a cathode connected to the first electrode and the second electrode, respectively.

12. The VOC detection sensor of claim 11, further comprising an ammeter measuring an amount of electrical charges flowing between the first electrode and the second electrode.

13. The VOC detection sensor of claim 5, further comprising an ammeter measuring an amount of electrical charges flowing between the first electrode and the second electrode.

14. A volatile organic compound (VOC) detection sensor, comprising:
 a transparent substrate;
 a light-emitting diode (LED) lamp installed or formed on a first side of the transparent substrate;
 a transparent electrode disposed on a second side of the transparent substrate;
 a metal electrode disposed to face the transparent electrode and spaced apart from the transparent electrode; and
 photoemission material disposed on a top surface of the transparent electrode or between the transparent electrode and the metal electrode, and receiving light radiated by the LED lamp and emitting photoelectrons,
 wherein the LED lamp provides light of a wavelength by which the photoelectrons are emitted from the photoemission material while the VOCs are not directly ionized.

* * * * *